United States Patent [19]

Erickson

[11] Patent Number: 4,824,527
[45] Date of Patent: Apr. 25, 1989

[54] NESTED ENRICHMENT CASCADE DISTILLATION OF UNEQUAL MIXTURES

[76] Inventor: Donald C. Erickson, 1704 S. Harbor La., Annapolis, Md. 21401

[21] Appl. No.: 872,558

[22] Filed: Jun. 10, 1986

[51] Int. Cl.$^4$ .............................................. B01D 3/14
[52] U.S. Cl. ........................................ 203/25; 203/27; 203/75; 203/77; 203/78; 203/80; 203/DIG. 8; 203/DIG. 9; 62/34
[58] Field of Search ...................... 203/75, 21, 25, 27, 203/71, 73, 77, 80, 78, DIG. 9, DIG. 8; 62/34, 24, 41, 23

[56] References Cited

U.S. PATENT DOCUMENTS

| | | | |
|---|---|---|---|
| 1,896,100 | 2/1933 | Ricard et al. | 203/15 |
| 2,699,046 | 1/1955 | Etienne | 62/31 |
| 3,277,655 | 10/1966 | Geist et al. | 62/29 |
| 3,327,489 | 6/1967 | Gauner, Jr. | 62/29 |
| 3,725,211 | 4/1973 | Gehrken et al. | 203/DIG. 19 |
| 4,210,495 | 7/1980 | Pinto | 203/22 |
| 4,246,073 | 1/1981 | Umeda et al. | 203/25 |
| 4,332,645 | 6/1982 | Müller et al. | 203/DIG. 19 |
| 4,340,447 | 7/1982 | Laverick et al. | 203/DIG. 19 |
| 4,422,903 | 12/1983 | Messick et al. | 203/19 |
| 4,428,799 | 1/1984 | Standiford | 203/19 |
| 4,541,897 | 9/1985 | Somma et al. | 203/19 |
| 4,566,947 | 1/1986 | Tsuruta | 203/DIG. 4 |
| 4,586,986 | 5/1986 | Preusser et al. | 203/25 |

FOREIGN PATENT DOCUMENTS

| | | | |
|---|---|---|---|
| 0132268 | 9/1978 | Fed. Rep. of Germany | 203/DIG. 19 |
| 2856051 | 7/1979 | Fed. Rep. of Germany | 203/DIG. 19 |
| 2035813 | 6/1980 | United Kingdom | 203/DIG. 4 |

OTHER PUBLICATIONS

C. J. King, "Separation Processes", McGraw Hill, 1980, 2nd ed., pp. 219 and 692-694.

Primary Examiner—David L. Lacey
Assistant Examiner—V. Manoharan

[57] ABSTRACT

A fractional distillation system is provided for fractionating unequal liquid mixtures with lower heat throughput and lower energy consumption. For mixtures in which the heavy fraction is predominant (FIG. 1), a stripper (2) pre-fractionates part of the mixture at lower pressure and at no extra energy cost by being reboiled by an intermediate condenser (3). The pre-fractionator temperature range is preferably nested within (overlapped by) the distillation column (6) temperature range.

8 Claims, 2 Drawing Sheets

NESTED ENRICHMENT CASCADE DISTILLATION OF UNEQUAL MIXTURES

DESCRIPTION

1. Technical Field

The present invention is directed to improving distillation efficiency and corresponding reducing the energy required for fractional distillation of liquid mixtures. The method allows the use of the same low heat source and heat sink temperatures as required in conventional simple distillation, and does not require complicated external heat recycling devices, such as heat pumps. Fractional distillation of liquid mixtures is the most common method of industrial separation of liquid mixtures.

2. Background of the Prior Art

A fractional distillation column or "fractionator" is comprised of at least one feed point for a fluid mixture, at least one zone of countercurrent vapor liquid contact, and at least two withdrawal points for products of the fractional distillation. If the zone of the countercurrent contact is all below the feed introduction point, the column may be called a stripping column, and conversely a rectifying column signifies that all the countercurrent contact is above the feed point. Reboil vapor can be generated by indirectly applying heat to column bottom liquid, and reflux liquid can be generated by applying cooling to (removing heat from) column overhead vapor.

It is known that providing part of the column reboil at an intermediate height causes the column to be more efficient, i.e., the operating line to be closer to the equilibrium line on a McCabe Thiele diagram. This is of limited value in those columns driven by heat: the total heat requirement remains the same, and the advantage of providing some of it at a slightly reduced temperature is offset by the complication and cost of providing two reboiling heat exchangers instead of only one. The same considerations apply to intermediate reflux condensers—the resulting increased column efficiency allows some of the heat to be withdrawn at a slightly higher temperature, but that small temperature advantage is usually not worth the added cost of the intermediate reflux condenser.

The fluid at the top or overhead end of a fractionator is also known as the light fraction or product, and that at the bottom as the heavy fraction. The light freaction is the more volatile fraction, and usually although not always has lower molecular weight, hence its name.

It is known to reduce the heat throughput required for distillation by using a dual pressure column, also known as a cascade. See, for example, C. J. King, 'Separation Processes', McGraw Hill, 1980, 2nd ed. p. 219 and 692–694. Although the heat throughput is decreased, the required temperature drop of the heat is substantially increased. In a cascade, the inherent efficiency of distillation is not improved; that is, somewhat more availability (ability to perform work) is extracted from the heat flowing through the cascade than from the heat flowing through a simple distillation column. A simple distillation is described as a single column with stripping section, rectifying section, single feed point, reboiler, reflux condenser, and two product withdrawals, one at each end.

When column temperature differential between overhead and bottom is small, the "dual heat use" aspect of cascades is very advantageous even though the distillation efficiency is not improved. However, for large $\Delta T$ columns the cascade requires a correspondingly large pressure ratio between the two columns. The high pressure column may entail increased capital costs from strength considerations, and usually has less favorable relative volatility. Conversely, the low pressure column may be driven into the vacuum region, adding cost and complication. Either the high pressure end temperatures are much higher, threatening thermal decomposition, or the low pressure end temperatures are much lower, possibly requiring refrigeration and risking freezeup. The large temperature differences across the cascade give added significance to the sensible heat of the various streams. And finally, most significantly, the substantially higher temperature level heat necessary to drive a full cascade as opposed to a simple column represents availability that usually is no longer available in carefully designed and heat integrated process plants.

A partial solution to the above problem in the case of unequal mixtures has been offered by enrichment cascades, also known as partial cascades. Whereas a full cascade is comprised of two simple distillation columns joined by a common reboiler/reflux condenser (R/R-C), the enrichment cascade is comprised of a single simple distillation column and only a rectifier or stripper in place of the second simple distillation column. Whereas the full cascade $\Delta T$ is the sum of two distillation column $\Delta T$'s plus the R/R-C $\Delta T$, the enrichment cascade $\Delta T$ is only the sum of one and one half column $\Delta T$'s plus the R/R-C $\Delta T$. The partial column can be connected to either the hot (bottom) or cold (overhead) end of the full column, and various feed regimens are possible. Examples of this approach are illustrated in U.S. Pat. No. 2,152,154.

The enrichment cascade, although an improvement, has the disadvantages that it only works well for unequal mixtures; that it still requires a considerably greater overall $\Delta T$ than a single column, and that there is essentially no increase in the single column efficiency.

U.S. Pat. No. 4,210,495 discloses two distillation columns which are heat integrated from the overhead of one to the feed of the other. U.S. Pat. No. 2,699,046 illustrates a variety of multiple (three or more) distillation column configurations incorporating a variety of intercondensers and interreboilers. U.S. Pat. Nos. 3,277,655 and 3,327,489 disclose processes for cryogenic distillation of gas mixtures in a dual pressure column configurations wherein feed gas is supplied to a preliminary rectifier which provides intermediate reboil to a distillation column. The temperature range of the rectifiers extends beyond that of the distillation column. U.S. Pat. No. 2,316,056 discloses various configuration of two or more distillation columns which are heat integrated at least in part by intermediate reboilers or reflux condensers. U.S. Pat. Nos. 1,896,100, 1,940,699, and 4,541,897 all present examples of two or more distillation columns interconnected by an interreboiler or intercondenser, but with each having a column temperature range which extends beyond that of theother column.

What is needed, and one object of this invention, is a means of reducing the amount of heat throughout required for liquid distillative separation without requiring a substantially increased source temperature or temperature drop of the throughput heat. That is, the reduced heat throughput advantage of an enrichment cascade is desired without the increased ΔT disadvantage.

DISCLOSURE OF INVENTION

The above and other useful advantages are obtained from process and/or apparatus for distilling liquid mixtures characterized by: first subjecting at least part of the mixture to a prefractionation in a stripper or a rectifier. For mixture containing a majority of the lighter, more volatile overhead product, the pre-fractionator should be comprised of a rectifier, whereas if the less volatile product predominates, the pre-fractionator should be comprised of a stripper. A partial stream of major product (at about the product purity specification) is withdrawn from one end of the pre-fractionator (top end of rectifier, bottom end of stripper), and fluid mixture enriched in the minor component is withdrawn from the other end. The enriched mixture plus any remaining feed mixture is then fed to a distillation column comprised of stripper, rectifier, reboiler, and condenser, operating at a pressure different from the pre-fractionator pressure. When the pre-fractionator is a rectifier, the distillation column is at a lower pressure, and for a stripper, the column is at a higher pressure. Intermediate height fluid from the distillation column is configured in heat exchange relationship with the fluid at the product end of the pre-fractionator whereby the heat flow (in the form of reboil vapor) that traverses the pre-fractionator also traverses at least one section of the distillation column (the section nearest the major product end). The minor product is withdrawn from one end of the distillation column, and the remaining major product is withdrawn from the other end.

With the pre-fractionator according to the above, the pre-fractionator ΔT is much smaller than the distillation column ΔT. Thus it is possible for the pre-fractionator to deliver heat to or remove heat from an intermediate location of the distillation column, thereby increasing the distillation column efficiency, without having the overall temperature range of the pre-fractionator exceed any part of the temperature range of the distillation column. Thus the same heat source that would reboil a simple column will reboil this nested enrichment cascade, and similarly the same cooling source as for simple distillation also serves for the NEC.

In essence, the separation achieved in the pre-fractionator is obtained at no energy cost—it is driven by energy which would otherwise be wasted in a simple distillation.

This disclosed NEC distillation will find greatest advantage when used to distill unequal mixtures, i.e., those having a minor component of 40% or less of the total, and mixtures having large boiling temperature difference between the light and heavy fractions, e.g., at least about 15° C. difference.

BEST MODE FOR CARRYING OUT THE INVENTION

Figure 1:
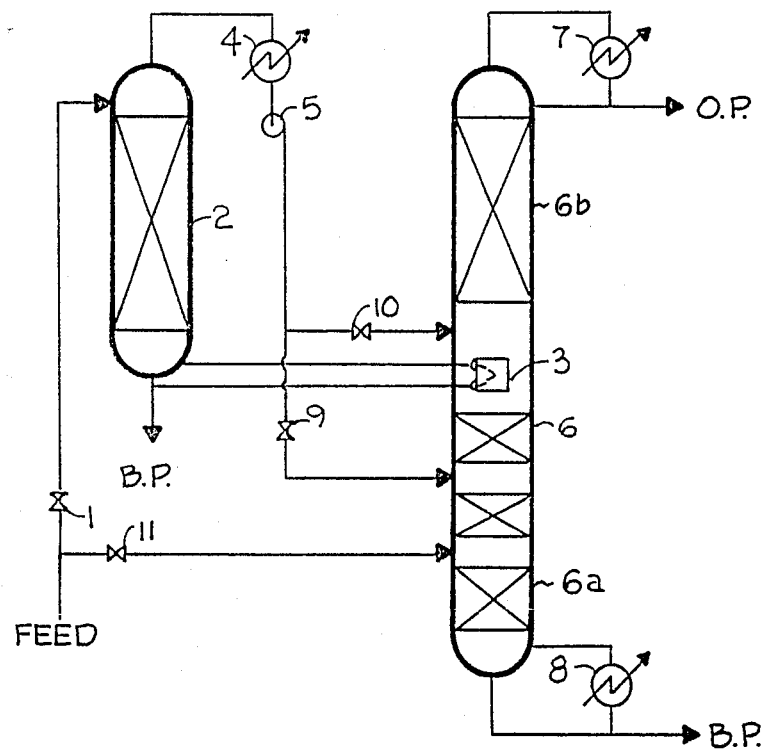
FIG. 1 is a schematic flowsheet depiction of the nested enrichment cascade configuration appropriate for distilling a liquid mixture in which the heavy fraction is predominant.

Referring to FIG. 1, at least part of the liquid feed mixture having a majority of heavy fraction is routed via control valve 1 to the overhead of stripping column 2. A first liquid product steam of the heavy (major) fraction is withdrawn from the bottom, part as product and part for reboiling in reboiler/intermediate reflux condenser 3. The vapor overhead, enriched in the light (minor) fraction relative to the feed composition, is withdrawn, condensed in cooler 4, and increased in pressure in a means for pressurization such as pump 5 (or a barometric leg if the height difference is sufficient). The enriched feed is then introduced into distillation column 6, which has an overhead reflux condenser 7, a bottoms reboiler 8, and the previously mentioned intermediate reflux condenser 3. Column 6 is comprised of stripping section 6a and rectifying section 6b. The enriched feed is preferably introduced through control valve 9 to a height of the distillation column having zones of countercurrent vapor liquid contact between the feed point and the intermediate refluxer 3, and also between the feed point and the reboiler 8. In limiting cases for nearly equal mixtures the enriched feed may alternatively be introduced via control valve 10 at the intercondenser height. Any remaining feed mixture is introduced to a lower height of column 6 than the enriched feed height, for example, through control valve 11. Liquid heavy product is withdrawn from both the stripper bottoms and the distillation column bottoms, and light product is withdrawn from the distillation column overhead. Thus the heat traversing up the lower sections of column 6 is split at intercondenser 3, with only part continuing up the column and the remainder diverted to reboil the stripper 2. The amount of feed to stripper 2 is regulated proportional to the amount of stripper reboil so as to maintain the desired purity of the stripper bottom product, and the remaining feed is routed to column 6 via valve 11. If feed pressure is not initially at stripper pressure, a feed pump will also be required in addition to or in lieu of valve 1.

Two variations of the above described embodiment are also of interest. First, the overhead vapor from stripper 2 can be increased in pressure via a compressor in lieu of condenser 4 and pump 5, and then introduced to column 6 as vapor. Secondly, the feed may be a two phase mixture, with only liquid phase being routed to stripper 2, while any vapor is routed through valve 11.

Figure 2:
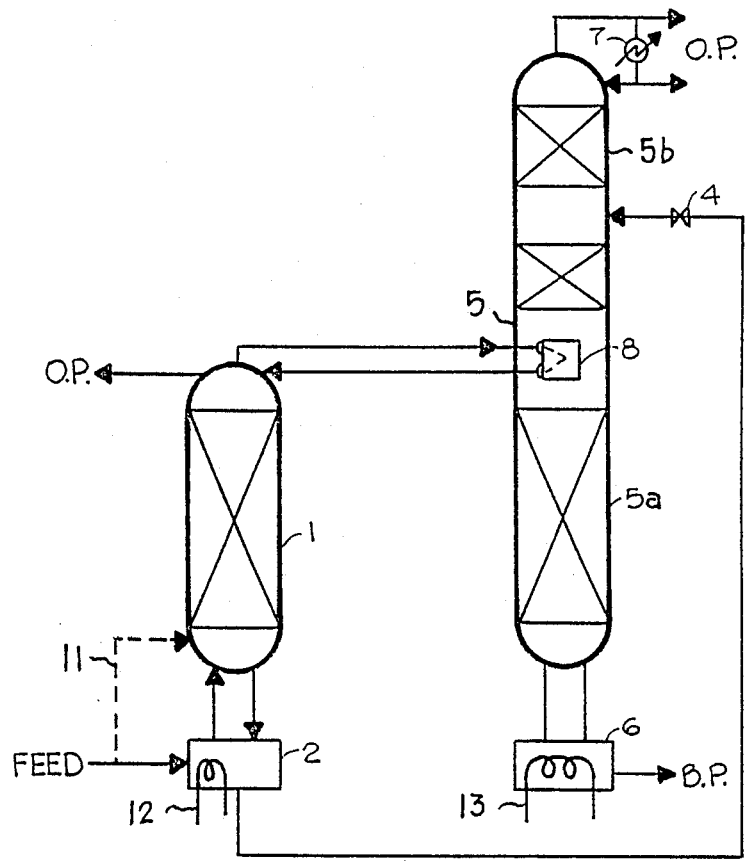
FIG. 2 is a corresponding flowsheet for a liquid mixture in which the light fraction is the major constituent.

FIG. 2 illustrates the NEC distillation embodiment for feed mixtures in which the light product is the major species. Preferably all of the feed is fed to the bottom of rectifier 1 via feed connection 11 (or equivalently to bottoms reboiler 2 heated by stream 12). The feed is rectified to a first stream of light (overhead) product which is withdrawn, and a bottom liquid mixture enriched in heavy product which is reduced in pressure by means for pressure reduction 4 and fed into distillation column 5 comprised of stripping section 5a and rectifying section 5b. Column 5 is reboiled by a source of heat 13 above ambient temperature at reboiler 6, and refluxed by reflux condenser 7, which may also be above ambient temperature. Intermediate reboil is provided by interreboiler 8 at a height no higher than the feed introduction height, and preferably below it. The light overhead product streams from rectifier 1 and column 5 may be withdrawn as either liquid or vapor phase. The heavy (minor) product is withdrawn from the bottom of column 5 (or equivalently from reboiler 6). Interreboiler 8 provides overhead reflux to rectifier 1. Reboilers 2 and 6 can be supplied by the same source of heat, at a temperature difference above column 5 bottom temperature which is less than the rectifier 1 ΔT.

For example, rectifier 1 operating pessure can be chosen such that the temperature range of rectifier 1 is wholly within the temperature range of column 5.

The various reboilers and reflux condenses including intermediate ones may either be located intenal to the columns or externally, as is known in the art. Various configurations of sensible heat exchange may be present between feed stream(s) and product streams, although as pointed out earlier those exchanger duties are not nearly as important with NEC distillation since the entire distillation is conducted over a much narrower temperature range, usually the same as for a simple distillation.

When extra temperature availability is present at the hot end (FIG. 2) or the cold end (FIG. 1), the pre-fractionator temperature range may be allowed to extend beyond the range of the distillation column to permit greater savings in heat throughput (as opposed to energy savings) and/or larger heat exchange $\Delta T$s on the interreboiler or intercondenser.

Surprisingly, even though the need for improved energy economy in distillation has been recognized for many years, and enrichment cascades have been known for over 46 years, and one special configuration of a nested enrichment cascade which is applicable to distillation of cryogenic gas mixtures has been known for over 20 years, nevertheless the unique advantages of nested enrichment cascades for liquid separations have never before been realized, nor has the process or apparatus necessary to achieve those advantages previously been disclosed.

The NEC distillation configuration may be combined with additional heat saving measures for even greater savings: e.g., compression heat pumps, absorption heat pumps, or additional stages of cascade.

As a numerical example of the benefits of NEC distillation of liquid mixtures, a computer simulation was run on a feed mixture liquid of 75 mole percent benzene, 25 mole percent toluene, at a feed rate of 100 gm mol/sec ("m") and a feed temperature of 96° C. at 135 kPa absolute. A conventional simple column with 20 theoretical trays and at a pressure of 135 kPa fractionated the feed to 75.5 m of 99% pure benzene and 24.5 m of 99% pure toluene at 91° C. and 123° C. respectively. The reboiler heat load was 1399 J/s, and the reflux condenser heat rejection was 1379 J/s. In contrast, a NEC distillation configuration having a 35 stage distillation column also at 135 kPa, plus an 18 stage rectifier at 255 kPa, has the same liquid feed also at 96° C. fed to the bottom of the rectifier. The rectifier products are 32 m of 99% benzene overhead at 113° C., and 68 m of 63.8 m/o benzene bottom liquid at 123° C. The latter stream is fed to tray 26 (from the bottom) of the distillation column, which is also interreboiled at tray 20 by the rectifier overhead. 24.7 m of bottom toluene (99% purity) and 43.3 m of overhead benzene (99.4% purity) is withdrawn from the distillation column. The rectifier reboiling duty is 694 J/s, the distillation column reboiler duty is 359 J/s, and the interreboiler duty is 578 J/s. Thus the total heat load necessary to drive the overall distillation is reduced from 1399 to 1053 J/s, a 25% savings, and the required heat input and rejection temperatures (123° C. and 91° C. respectively) have not changed.

A second computer simulation example illustrates the use of the FIG. 1 embodiment. 100 gm-mol/sec of a liquid mixture of 15 m/o n-butane, 85 m/o isopentane at 550 kPa and the bubble point is to be fractionated to 99% purity products. A simple distillation column at 550 kPa with 35 stages and the feed to stage 20 required 569 J/s reboiler duty at above 89° C. In the NEC configuration of FIG. 1, half the feed (50 m) is sent to a 20 stage stripper at 310 kPa and with an operating temperature range of 57° C. (overhead) to 65° C. (bottoms). 24.9 m of pentane bottom product is withdrawn, and the remaining 25.1 m of mixture containing 29% butane is fed to stage 16 of a 40 stage column at 550 kPa. The remaining 50 m of original feed is fed to tray 9. An intermediate reflux condenser at tray 24 provides bottoms reboil to the stripper. The distillation column reboiler duty is 419 J/s, or a 26% savings compared to the simple column.

In addition to the debutanizer ($C_4$–$C_5$-splitter) and benzene-toluene splitter examples above, other distillations which will benefit from the disclosed improvement include deethanizer, depropanizer, depentanizer, toluene-xylene, methanol-water, heptane-benzene, water-acetic acid, benzene-ethylbenzene, ethylene oxide-water, cumene-phenol, ethylbenzene-p-xylene, ethylbenzene-diethylbenzene, benzene-cumene, ethylene glycol-diethyleneglycol, phenol-acetophenone, and various nitriles and halocarbons (e.g., dichloroethane-trichloroethane or vinyl chloride monomer). This list is not exhaustive but merely indicative.

Although NEC distillation requires an added fractionator complete with at least one of reboiler and reflux condenser (and usually both), the added column increases the feed capability, i.e., can be used to debottleneck a column (at no energy cost). The NEC distillation decreases the required vapor and liquid flowrates in the columns sufficiently that even though a larger number of stages is required, there will usually nonetheless be lower average residence time and liquid holdup than in simple distillation. This is important for products subject to thermal decomposition (styrene) or for faster startups and transients.

I claim:

1. A method for fractionating a liquid mixture comprised of unequal amounts of major and minor product fractions, wherein the product fraction present in greater amount is the major product and that in lesser amount is the minor product, comprising:
   (a) pre-fractionating at least part of the liquid mixture in a pre-fractionator to a first major product stream and an enriched liquid stream enriched in the said minor product;
   (b) feeding the enriched liquid stream to a distillation column which is operating at a pressure different from the pressure of the pre-fractionator;
   (c) distilling the enriched liquid stream to a second major product stream and to said minor product stream;
   (d) exchanging latent heat between a fluid from the end of the pre-fractionator from which the first major product stream is obtained, and an intermediate height fluid of the distillation column;
   (e) reboiling said distillation column by a source of heat above ambient temperature; and
   (f) withdrawing said first major product stream from the pre-fractionator and said second major product stream from the distillation column.

2. Method according to claim 1 wherein said second major product stream is withdrawn from the overhead of said distillation column, the pre-fractionator is a rectifier operating at a higher pressure than the distillation column, and further comprising:

(a) feeding said at least part of the liquid mixture to the bottom of the rectifier;
(b) reboiling said rectifier;
(c) reducing the pressure of said enriched liquid stream before feeding it to the distillation column; and
(d) condensing said second major product stream from said distillation column by indirect heat exchange with a cooling fluid.

3. Method according to claim 1 wherein said first major product stream is obtained from the overhead of said pre-fractionator, which is a rectifier, and wherein a rectifier reflux liquid and a distillation column intermediate reboil is provided from the step 1(d) process.

4. Method according to claim 1 wherein said second major product stream is withdrawn from the bottom of said distillation column, and said first major product stream is withdrawn from the bottom of the pre-fractionator which is a stripper operating at a lower pressure than the distillation column, and further comprising:
(a) feeding said at least part of the liquid mixture to the overhead of the stripper;
(b) condensing an overhead vapor from the stripper to obtain said enriched liquid and increasing the pressure of the enriched liquid before feeding said enriched liquid to the distillation column;
(c) reboiling the stripper by the step 1(d) process.

5. A process for fractionally distilling a fluid mixture consisting essentially of a major amount of heavy product and a minor amount of light product comprising:
(a) feeding at least part of the fluid mixture to a pre-fractionator comprised of at least a stripping section;
(b) fractionating said pre-fractionator feed to a first heavy product stream as the bottom product and overhead fluid enriched in the minor product;
(c) increasing the pressure of the overhead fluid product and feeding said pressurized fluid to a distillation column comprised of stripping and rectifying sections; and
(d) reboiling the pre-fractionator by exchanging latent heat between an intermediate height vapor of said distillation column and a bottom liquid of said pre-fractionator.

6. Process according to claim 5 wherein said fluid mixture is liquid phase and further comprising condensing said enriched overhead fluid before increasing the pressure.

7. Processing according to claim 5 wherein said fluid mixture is vapor phase and further comprising compressing said pre-fractionator overhead to increase the pressure.

8. A process for fractionally distilling a fluid mixture consisting essentially of a major amount of light product and a minor amount of heavy product comprising:
(a) feeding the fluid mixture to the bottom of a rectifier;
(b) reboiling the rectifier by heat exchange to bottom liquid in a reboiler;
(c) rectifying the feed to a first light product overhead stream and an enriched bottom liquid;
(d) feeding said enriched bottom liquid at reduced pressure to a distillation column, and distilling said enriched bottom liquid to a second light product overhead stream and a heavy product bottom stream;
(e) exchanging latent heat from said first light product overhead vapor of said rectifier to intermediate height liquid of said distillation column, thereby providing rectifier reflux and a distillation column intermediate reboil;
(f) withdrawing said first light product stream from the rectifier overhead and withdrawing said second light product overhead stream from the distillation column overhead; and
(g) reboiling the distillation column.

* * * * *